(12) United States Patent
Engqvist et al.

(10) Patent No.: US 8,591,645 B2
(45) Date of Patent: Nov. 26, 2013

(54) HYDRAULIC CEMENTS WITH OPTIMIZED GRAIN SIZE DISTRIBUTION, METHODS, ARTICLES AND KITS

(75) Inventors: Håkan Engqvist, Östhammar (SE); Jonas Åberg, Uppsala (SE)

(73) Assignee: OssDsign AB, Uppsala (SE)

( * ) Notice: Subject to any disclaimer, the term of this patent is extended or adjusted under 35 U.S.C. 154(b) by 107 days.

(21) Appl. No.: 13/229,545

(22) Filed: Sep. 9, 2011

(65) Prior Publication Data

US 2013/0066325 A1    Mar. 14, 2013

(51) Int. Cl.
   *C04B 12/02*    (2006.01)
   *A61B 17/56*    (2006.01)
   *A61K 6/06*    (2006.01)

(52) U.S. Cl.
   USPC ............... 106/691; 106/35; 106/690; 606/92

(58) Field of Classification Search
   USPC .............................. 106/35, 691, 690; 606/92
   See application file for complete search history.

(56) References Cited

U.S. PATENT DOCUMENTS

| | | | |
|---|---|---|---|
| 5,152,836 A | 10/1992 | Hirano et al. | |
| 5,338,356 A | 8/1994 | Hirano et al. | |
| 5,605,713 A | 2/1997 | Boltong | |
| 5,683,667 A | 11/1997 | Fulmer et al. | |
| 5,782,971 A | 7/1998 | Constantz et al. | |
| 5,783,217 A | 7/1998 | Lee et al. | |
| 6,117,456 A | 9/2000 | Lee et al. | |
| 6,206,957 B1 | 3/2001 | Wenz et al. | |
| 6,338,810 B1 | 1/2002 | Carpena | |
| 6,521,246 B2 | 2/2003 | Sapieszko et al. | |
| 6,642,285 B1 | 11/2003 | Bohner et al. | |
| 6,733,582 B1 | 5/2004 | Bohner et al. | |
| 6,863,899 B2 | 3/2005 | Koblish et al. | |
| 6,905,516 B1 * | 6/2005 | Lemaitre et al. | 623/23.56 |
| 6,991,803 B2 | 1/2006 | Sapieszko et al. | |
| 7,118,705 B2 | 10/2006 | Lin | |
| 7,175,858 B2 | 2/2007 | Constantz et al. | |
| 7,252,841 B2 | 8/2007 | Constantz et al. | |
| 7,318,841 B2 | 1/2008 | Tofighi et al. | |
| 7,351,280 B2 | 4/2008 | Khairoun et al. | |
| 7,407,542 B2 | 8/2008 | Lemaitre et al. | |
| 7,473,312 B2 | 1/2009 | Barralet et al. | |
| 7,501,018 B2 | 3/2009 | Engqvist et al. | |
| 7,709,029 B2 * | 5/2010 | Chow et al. | 424/602 |
| 7,754,246 B2 | 7/2010 | Mosley et al. | |
| 8,282,396 B2 * | 10/2012 | Chow et al. | 433/215 |
| 2003/0082232 A1 | 5/2003 | Lee et al. | |
| 2003/0199615 A1 | 10/2003 | Chaput et al. | |
| 2006/0239884 A1 | 10/2006 | Chane-Ching et al. | |
| 2006/0263443 A1 | 11/2006 | Chow et al. | |
| 2007/0092856 A1 | 4/2007 | Chow et al. | |
| 2007/0189951 A1 | 8/2007 | Constantz et al. | |
| 2008/0027455 A1 | 1/2008 | Bondeville | |
| 2008/0028992 A1 | 2/2008 | Lee et al. | |
| 2008/0187571 A1 | 8/2008 | Clineff et al. | |
| 2008/0206300 A1 | 8/2008 | Bohner et al. | |
| 2009/0022771 A1 | 1/2009 | Lynn et al. | |
| 2009/0220475 A1 | 9/2009 | Bohner et al. | |
| 2010/0095870 A1 | 4/2010 | Insley et al. | |
| 2010/0269736 A1 | 10/2010 | Chow et al. | |
| 2010/0303888 A1 | 12/2010 | Barralet et al. | |
| 2011/0014244 A1 | 1/2011 | Sapieszko et al. | |
| 2011/0152195 A1 | 6/2011 | O'Mahony et al. | |
| 2011/0158963 A1 | 6/2011 | Font Perez et al. | |
| 2012/0058152 A1 | 3/2012 | Garcia De Castro Andrews et al. | |
| 2013/0138114 A1 | 5/2013 | Lin et al. | |

FOREIGN PATENT DOCUMENTS

| | | |
|---|---|---|
| CN | 1919357 A | 2/2007 |
| EP | 543765 A1 | 5/1993 |
| EP | 1023032 B1 | 1/2002 |
| EP | 936929 B1 | 6/2004 |
| EP | 1380313 B1 | 5/2005 |
| EP | 1298103 B1 | 5/2011 |
| JP | 1-100049 A | 4/1989 |
| WO | 02/11781 A1 | 2/2002 |
| WO | 2004/093734 A2 | 11/2004 |
| WO | WO 2004093734 A2 * | 11/2004 |
| WO | 2005/074453 A2 | 8/2005 |
| WO | 2005/077049 A2 | 8/2005 |
| WO | 2007/047921 A2 | 4/2007 |
| WO | 2009/077210 A1 | 6/2009 |
| WO | WO 2010055483 A2 * | 5/2010 |
| WO | 2010/092001 A1 | 8/2010 |
| WO | 2011/009635 A1 | 1/2011 |

OTHER PUBLICATIONS

Bohner et al, J. Biomaterials, 26(33):6423-6429 (2005).
Xu et al, Journal of Materials Science: Materials in Medicine, 18(7):1345-1353 (2007).
Barralet et al, J. Biomaterials, 25(11):2197-2203 (2004).
Habraken et al, Advance Drug Delivery Reviews, 59(4-5):234-248 (2007).
Han et al, Acta Biomaterialia, 5:3165-3177 (2009).
Desai et al, Advances in Bioceramics and Biocomposites II, Ceramic Engineering and Science Proceedings, vol. 27, Issue 6, Wereszczak et al, Editor, Wiley, pp. 61-69 (Nov. 2006).
Hirayama et al, Journal of Research of the National Institute of Standards and Technology, 113(6):311-320 (2008).

* cited by examiner

*Primary Examiner* — Anthony J Green
(74) *Attorney, Agent, or Firm* — Porter Wright Morris & Arthur LLP

(57) ABSTRACT

A non-aqueous hydraulic cement composition comprises a non-aqueous mixture of (a) β-tricalcium phosphate powder, (b) monocalcium phosphate powder, and (c) non-aqueous water-miscible liquid, wherein (i) at least about 90% of the monocalcium phosphate powder has a grain size in a range of about 200-600 μm and the powder (weight) to liquid (volume) ratio is about 2.5-5.5, (ii) at least about 90% of the monocalcium phosphate powder has a grain size in a range of about 1-400 μm and the powder (weight) to liquid (volume) ratio is about 2-5, or (iii) at least about 90% of the monocalcium phosphate powder has a grain size in a range of about 1-600 μm and the powder (weight) to liquid (volume) ratio is about 2.5-5.5. Methods, hardened cements, articles of manufacture and kits employ such compositions.

22 Claims, 2 Drawing Sheets

HYDRAULIC CEMENTS WITH OPTIMIZED GRAIN SIZE DISTRIBUTION, METHODS, ARTICLES AND KITS

FIELD OF THE INVENTION

The present invention is directed to hydraulic cements, and, more particularly, to non-aqueous hydraulic cement compositions or partly aqueous compositions. The hydraulic cement compositions may be formed into hardened cements by contact with a hydration liquid or vapor. In a specific embodiment, the hydraulic cements are suitable for use as biomaterials for in vivo delivery, for example for bone and tooth-root restoration. The invention is also directed to hardened cements formed from such hydraulic cement compositions and to methods of producing hardened cements. The invention is further directed to kits and articles of manufacture including, inter alia, such hydraulic cement compositions.

BACKGROUND OF THE INVENTION

Self-hardening calcium phosphate cements (CPC) have been used for bone and tooth restoration and for local drug delivery applications. See, for example, Larsson et al, "Use of injectable calcium phosphate cement for fracture fixation: A review," *Clinical Orthopedics and Related Research*, 395:23-32 (2002) and Oda et al, "Clinical use of a newly developed calcium phosphate cement (XSB-671D)," *Journal of Orthopedic Science*, 11(2):167-174 (2006). The cements in powder form are typically mixed with an aqueous solution immediately before application. In the clinical situation, the ability of the surgeon to properly mix the cement powder and hydrating liquid and then place the cement paste in a defect within the prescribed time is a crucial factor in achieving optimum results. Specifically, the dry cement powder material needs to be mixed with an aqueous solution in the surgical setting, i.e., the operating room, transferred to an applicator, typically a syringe, and delivered to the desired location within the setting time. Conventional cements generally have a setting time of about 15-30 minutes. However, the methods used for mixing and transfer of cement for injection in the operating room are technically difficult and pose a risk for non-optimal material performance, e.g., early setting renders materials difficult to inject or causes phase separation, so-called filter pressing. Further, for technical reasons and time constraints, the material is typically mixed with a hydrating liquid in bulk to form a paste and the paste is then transferred to smaller syringes for delivery. In practice, material is often wasted due to an early setting reaction, i.e., the hydrated material sets to a hardened cement prior to delivery to the desired location, or because too much material is being mixed. A solution to these problems that includes the possibility to deliver material in smaller quantities in a more controlled manner is thus desired.

The problem of obtaining a proper mix of the powder material and hydrating liquid for optimum clinical results in apatite cements has been addressed in US 2006/0263443, US 2007/0092856, Carey et al, "Premixed rapid-setting calcium phosphate composites for bone repair," *Biomaterials*, 26(24):5002-5014 (2005), Takagi et al, "Premixed calcium-phosphate cement pastes," *Journal of Biomedical Materials Research Part B-Applied Biomaterials*, 67B(2):689-696 (2003), Xu et al, "Premixed macroporous calcium phosphate cement scaffold," *Journal of Materials Science-Materials in Medicine*, 18(7):1345-1353 (2007), and Xu et al, "Premixed calcium phosphate cements: Synthesis, physical properties, and cell cytotoxicity," *Dental Materials*, 23(4):433-441 (2007), wherein premixed pastes are described. In US 2006/0263443, for example, a powder composition for hydroxyapatite is premixed with an organic acid and glycerol to form a paste, which paste may subsequently be injected into a defect. The injected material hardens via the diffusion of body liquids into the biomaterial. The organic acid is added to increase resistance to washout and the end product after setting is apatite, which is known to have a long resorption time in vivo as described above. Also, compositions of β-tricalcium phosphate (β-TCP) and hydrated acid calcium phosphate in glycerin or polyethylene glycol have previously been described in CN 1919357. Han et al, "β-TCP/MCPM-based premixed calcium phosphate cements," *Acta Biomaterialia*, doi:10.1016/j.actbio.2009.04.024 (2009) and Aberg et al, "Premixed acidic calcium phosphate cement: characterization of strength and microstructure, *Journal of Biomedical Materials Research*, 93(2):436-41 (May 2010). Thus, one objective of the prior art has been to provide a formulation consisting of one phase. However, it is often difficult to optimize such formulations for biological response and bone in-growth. Additionally, handling premixed formulations can be problematic if they are too viscous to deliver by injection.

Thus, there is a continuing need to be able to efficiently prepare and safely deliver hydraulic cements, particularly for biomedical applications, i.e., hydraulic cements that overcome the above noted and/or other difficulties of conventional hydraulic cement materials, while optionally optimizing performance properties.

SUMMARY OF THE INVENTION

Accordingly, it is an object of the present invention to provide hydraulic cements, and hardened cements, methods, kits and articles of manufacture based on the hydraulic cements, with an optimized handling and biological response for clinical use.

In one embodiment, the invention is directed to a non-aqueous, hydraulic cement composition which comprises a non-aqueous mixture of (a) β-tricalcium phosphate powder, (b) mono calcium phosphate (MCP), and (c) non-aqueous water-miscible liquid. In said embodiment, the MCP grain size is chosen to obtain specific properties, e.g. higher injectability (large grained powder) or better mechanical properties (fine grained precursor powder). The MCP powder represents the unreacted powder in the paste that reacts with water to form a hardened material. MCP stands for mono calcium phosphate and may be in the form of mono calcium phosphate monohydrate (MCPM) or anhydrous mono calcium phosphate (MCPA) or combinations thereof. In specific embodiments, the MCP comprises a majority of, consists essentially of, or consists of, respectively, MCPA.

The invention is also directed to methods of producing a hardened cement with such compositions, hardened cements produced from such compositions, kits including such compositions, and articles of manufacture including such compositions.

The hydraulic cement compositions according to the invention are advantageous in that they avoid many of the preparation difficulties of conventional hydraulic cement compositions, particularly when used as biomaterials, and may be easily and efficiently delivered to a desired location, without excessive material waste. Additionally, the hydraulic cement compositions according to the invention may be optimized for improved performance properties regarding handling, pore size distribution and biological response. These and additional objects and advantages of the present invention will be more fully appreciated in view of the following detailed description.

BRIEF DESCRIPTION OF THE DRAWINGS

The following detailed description will be more fully understood when viewed together with the drawings, in which:

FIG. 1A: >100 μm; FIG. 1B: 100-200 μm; FIG. 1C: 200-400 μm; FIG. 1D: 400-600 μm; FIG. 1E: All sizes (no separation). In the materials of FIG. 1C and FIG. 1D, where larger grain sizes have been used, larger pores are clearly visibly throughout the set cement, whereas the materials of FIG. 1A and FIG. 1B have smaller pores.

DETAILED DESCRIPTION

Figure 1A:
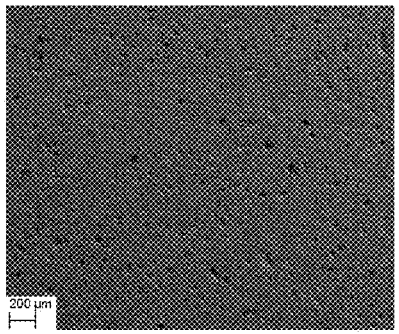
FIGS. 1A-1E show scanning electron micrograph (SEM) images (75×) of polished cross sections of hardened cement samples as described in Example 1, prepared using a powder to liquid (P/L) ratio of 4.2. The monocalcium phosphate (MCP) grain size is as follows.
Figure 1B:
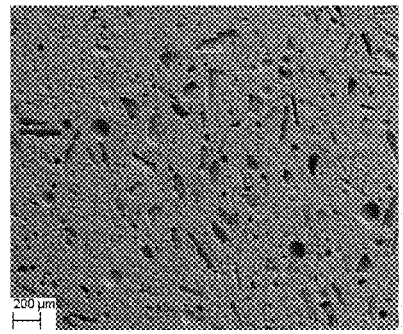
Figure 1C:
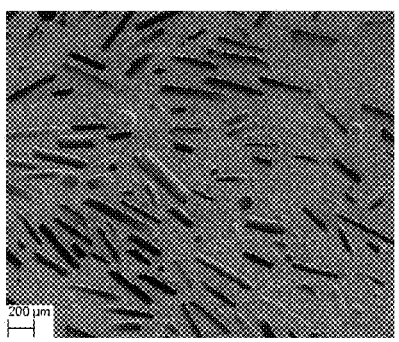
Figure 1D:
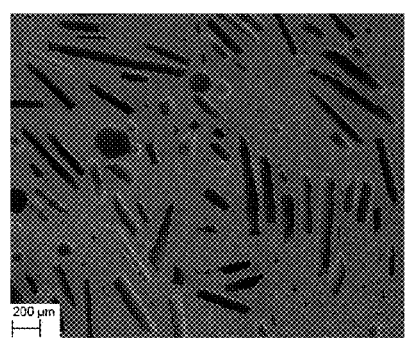
Figure 1E:
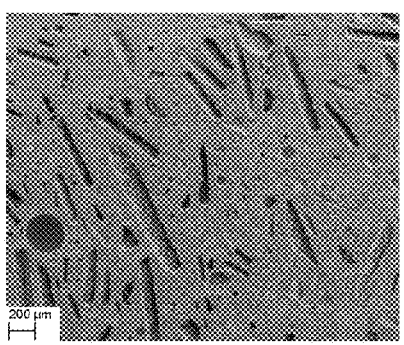

The non-aqueous, hydraulic cement compositions of the present invention are suitable for use in various biomedical applications. The present description refers to use of the compositions for in vivo applications, for example in bone and tooth repair. It will be appreciated that the present compositions are suitable for other in vivo applications as well as for non-biomaterial applications. The compositions of the invention contain non-hydrated powder and will hydrate upon contact with a hydrating liquid or vapor, typically water, body fluids or other aqueous solution. In a first embodiment, the monocalcium phosphate (MCP) powder composition comprises monocalcium phosphate monohydrate (MCPM), or anhydrous monocalcium phosphate MCPA, or a mixture thereof.

The powder composition further comprises β-tricalcium phosphate, and may further comprise one or more additional basic calcium phosphates. In a specific embodiment, the pH of the hydraulic cement composition during setting is less than about 6.0 to result in the Brushite or Monetite cement. Thus, the Brushite or Monetite-forming calcium phosphate powder composition may further comprise one or more calcium phosphates selected from the α-tricalcium phosphate, amorphous calcium phosphate, and tetracalcium phosphate.

Generally, aqueous cement compositions mixed with water benefit from smaller particle sizes in the powder composition since this gives faster setting time, stronger cements and better injectability. However, it has been discovered that premixed cements are affected differently. Smaller particle sizes make the cements viscous, but if the particle sizes are too small, the cements can not be delivered by injection. For premixed cements, the setting time is not affected to the same extent since, in addition to the dissolution rate, the diffusion rate of water into the cement also controls the setting process. Larger particles make the cement easier to inject as compared with cement formed using finer particle size powders. While not intending to be bound by theory, it is believed that this is the result of more liquid, i.e., glycerol, on average, between each powder grain for large grain sizes, resulting in an easier shear of the cement paste, making the cement easier to inject. In addition, it is important to be able to control the porosity since the porosity affects bone ingrowth and the resorption time in vivo, Ginebra et al "In vivo evaluation of an injectable Macroporous Calcium Phosphate Cement" *Journal of Materials Science-Materials in Medicine,* 18(2):353-361 (2007). By controlling the MCP particle size, it is possible to control the porosity in the cement. In previous cement formulations, additional additives were needed in order to obtain the desired porosity. Furthermore, in conventional water-mixed cements, the hardening proceeds without any substantial liquid exchange since the water present in the cement is enough for the hardening to occur. For the cements in the present invention, a liquid exchange must occur between the non-aqueous water-miscible liquid in the cement and hydrating liquid or vapor, for example, added water of a surrounding body fluid, i.e., saliva, blood, etc., as the hydrating liquid or vapor is needed to start the setting reaction. During this liquid exchange in vivo, biological components will be transported into the cement, which are beneficial for faster bone ingrowth and resorption of the cement. This liquid exchange will benefit from larger particle sizes that allow a quicker liquid exchange during hardening through the larger pores, which are formed when the MCP dissolves and since there is more glycerol (on average) between each powder grain.

The invention is specifically directed to a non-aqueous, hydraulic cement composition comprising a non-aqueous mixture of (a) β-tricalcium phosphate powder (β-TCP), (b) mono calcium phosphate powder, and (c) non-aqueous water-miscible liquid.

In specific embodiments, the relation between components (a) and (b) is about 1:4-4:1, more specifically about 1:3-3:1, or more specifically about 2:3-3:1, to obtain a cement with higher mechanical strength.

The β-TCP particle size can also be used to control properties. β-TCP has a lower solubility than MPC and the particle size of the β-TCP is therefore preferably smaller than the particle size of the MCP. Larger β-TCP particles make the cement easier to inject than finer particle size powders. Smaller particles will dissolve faster and thus allow a faster setting and the set cement will become stronger. The mean particle size of the β-TCP is preferably 1 to 40 μm, more preferably 3 to 30 μm and most preferably 5 to 25 μm. The particle size distribution can for example be determined using laser diffraction.

In the powder composition, the MCP particle size can be used to tailor the handling properties, the porosity of the hardened body and the mechanical strength of the hardened body, e.g.:

1. The MCP particle size is about 200-600 μm, more specifically about 400-600 μm, and the powder (weight) to liquid (volume) ratio (P/L) (for example, in g/ml) is about 2.5-5.5, more specifically about 3.5-5, to obtain a porous cement upon hardening allowing for faster bone ingrowth.

2. The MCP particle size is about 1-400 μm, more specifically about 10-200 μm, and more specifically about 10-100 μm, and the P/L is about 2-5, more specifically about 3-4.5, for a cement with higher mechanical strength.

3. The MCP particle size range is wide, about 1-600 μm, and the P/L is about 2.5-5.5, more specifically about 3.5-5, for cement with some larger pores allowing fast diffusion and that is mechanically strong.

In said compositions, the specific particles sizes can for example be obtained by sieving and >90%, or more specifically, >95% the powder weight is within the specified range.

In all embodiments of the invention as described above, any suitable, non-aqueous water-miscible liquid may be employed. Exemplary liquids include, but are not limited to, glycerol, propylene glycol, poly(propylene glycol), poly(ethylene glycol) and combinations thereof, and related liquid compounds and derivatives, i.e., substances derived from non-aqueous water miscible substances, substitutes, i.e., substances where part of the chemical structure has been substituted with another chemical structure, and the like. Certain alcohols may also be suitable. In a specific embodiment, the liquid is glycerol.

The hydraulic cement compositions of the invention may also include one or more porogens to provide an additional porosity to the cement product. The porogen may include sugars and other fast-resorbing agents, and non-limiting examples include calcium sulphate, mannitol, poly(a-hydroxy ester) foams, sucrose, $NaHCO_3$, NaCl and sorbitol. The amount of porogen may suitably be from about 5 to about 30 weight % of the powder composition. The grain size of the porogens are typically in the range of 50 to 600 µm.

Optionally, the cement composition of the invention may also include porous granules. The porous β-TCP granules modify the resorption rate and bone remodeling of the hardened cement, which is formed upon hydration and setting. The granules generally comprise agglomerated powders and the porosity of the granules comprises pores formed between individual powder grains in the agglomerates. In a specific embodiment, the granule size is from about 10 to about 3000 micrometers. In a further embodiment, the granule size is from about 10 to about 1000 micrometers and may be selected to optimize mechanical and/or biological properties of the resulting hardened cement. In a specific embodiment, the granule porosity is at most 80 vol % and the pore size is at most 200 micrometers. In a specific embodiment, the weight ratio of porous β-TCP granules to additional calcium phosphate powder in the non-hydrated powder composition is in a range about 1:6 to about 1:1, or, more specifically, in a range of about 1:9 to about 4:6.

The hydraulic cement compositions in the form of a premixed paste may be delivered, for example to an implant site when used as a biomaterial, using a syringe or spatula. The hydraulic cement compositions may be shaped in vivo, and subsequently be hydrated or be allowed to hydrate in vivo. Optionally, a water-containing liquid can be added to the premixed paste before delivery, for example, before injection. This may be achieved by use, for example, of a double-barrel syringe with the described premixed paste in one and the hydrating liquid, e.g. water or a water-containing liquid, in the other. Optionally pre-cursor powders are mixed in both barrels. The two pastes may then be mixed using a mixing tip during injection.

The hydraulic cement compositions in the form of a premixed paste can also be packaged in a vacuum package to reduce the amount of air voids in the paste and thus increase the final strength of the hardened material. Air voids reduce the strength of the set material and reduction of air voids is therefore important. The hydraulic cement compositions may be conveniently mixed and packaged under vacuum conditions. Preferably the hydraulic cement compositions are vacuum-mixed (e.g. in a Ross Vacuum Mixer Homogenizer).

In another embodiment of the invention, the hydraulic cement compositions may be provided as a component of a kit, for example in combination with a separately contained quantity of hydrating liquid. In a specific embodiment, the kit comprises several prefilled syringes of the same or of various sizes. One non-limiting example is a kit with several 2 ml prefilled syringes. Another non-limiting example is a kit with several 1 ml prefilled syringes. Thus, another embodiment of the invention comprises an article of manufacture comprising a hydraulic cement composition in a dispensing container, more specifically a syringe. In another example the cement composition is provided in a jar, then the cement is preferably applied using a special device, for example, a spatula or a spoon.

The described hydraulic cement compositions are suitably employed as injectable in situ-setting biomaterials. The compositions can be used as any implant, more specifically as a bone implant, more specifically as dental or orthopedic implant. In a specific embodiment, the hydraulic cement compositions are suitably used as material in cranio maxillo-facial defects (CMF), bone void filler, trauma, spinal, endodontic, intervertebral disc replacement and percutaneous vertebroplasty (vertebral compression fracture) applications.

Various embodiments of the invention are illustrated in the following Examples.

Example 1

The example shows how properties such as injectablity, compressive strength and porosity can be controlled by varying the MCP particle size. By using a smaller a particle size, the injection force increases as well as the compressive strength whereas the porosity of the set cement decreases. Inversely, by using a larger particle size, the injection force decreases as well as the compressive strength and the pore size distribution of the cement shifts towards larger pores.

Cement Preparation

The cement consisted of monocalcium phosphate (MCP, Alfa Aesar) and β-tricalcium phosphate, mean particle size 12.9 µm measured by laser diffraction (β-TCP, Sigma), in a molar ratio of 1:1. The MCP was sieved in order to obtain the following particle sizes; <100 µm, 100-200 µm, 200-400 µm, and 400-600 µm. MCP was also used as received, containing all the mentioned particle sizes as well <5% of particles larger than 600 µm, hereby referred to as ALL. Glycerol (anhydrous) was used as mixing liquid. A vacuum mixer was used to mix the cements.

The evaluated cement mixtures are listed in Table 1:

TABLE 1

Cement Mixtures

| Particle size (µm) | P/L (g/ml) |
| --- | --- |
| <100 | 3.8, 4.2 |
| 100-200 | 4.0, 4.2 |
| 200-400 | 4.2 |
| 400-600 | 4.2, 4.4 |
| ALL | 4.2 |

Injectability

The injectability was evaluated by measuring the force needed to inject 2 ml of cement paste from a disposable syringe; barrel diameter 8.55 mm, outlet diameter 1.90 mm. The force applied to the syringe during the injection was measured and mean injection force from 10 to 30 mm displacement was calculated, this force is referred to as the injection force.

Hardening Depth

The hardening depth of the cement after 50 minutes was evaluated on two cements, with particle sizes of 100-200 µm and 400-600 µm. The cements were injected into cylindrical split moulds, diameter 6 mm, height 12 mm open at one end, and immersed in 50 ml PBS at 37° C. After 50 min, the mould halves were separated and the thickness of the hardened surface layer was measured using a micrometer calliper.

Compressive Strength (CS)

For CS measurements, the paste was injected into cylindrical moulds and immersed in 50 ml PBS at 37° C. in a sealed beaker. Sample dimensions were diameter 6 mm and height 12 mm. After 24 h, the samples were removed from the moulds. Thereafter, the maximum compressive stress until failure was measured using a universal testing machine.

Scanning Electron Microscopy (SEM)

SEM analysis was made of the cross-sections of hardened cement to study the pore structure.

The results are set forth in Table 2:

TABLE 2

Results

| Grain size (μm) | P/L (g/mL) | Injection force (N) | Hardening depth (mm) | Compressive strength (MPa) |
|---|---|---|---|---|
| <100 | 3.8 | 90 ± 10 | | 10-12 |
| <100 | 4.2 | 200 ± 10 | 1.55 | 12-14 |
| 100-200 | 4.0 | 75 ± 10 | | 9-11 |
| 100-200 | 4.2 | 150 ± 10 | | 10-12 |
| 200-400 | 4.2 | 75 ± 10 | | 8-10 |
| 400-600 | 4.2 | 60 ± 10 | 1.77 | 6-8 |
| 400-600 | 4.5 | 160 ± 10 | | 7-9 |
| ALL | 4.2 | 80 ± 10 | | 11-13 |

Example 2

This example shows how the addition of mannitol to the cement composition affects the porosity, setting time and mechanical properties of the set cement. With no added mannitol, the porosity of the set cement is 50%, and with the addition of 30% mannitol, the porosity increases to ~70%. The results show that it is possible to control the porosity of the set cement via addition of pore forming agents. The cement is intended to be used either as in vivo injectable material or to harden in molds outside the body and then implanted in hardened form.

Cement Preparation

The cement consisted of an equimolar mixture of mono calcium phosphate (MCP, Alfa Aesar) and β-tri calcium phosphate (Sigma). Glycerol was used as mixing liquid. Mannitol was used as the porogen, particle size <400 μm. The mannitol powder was combined with the premixed powder at mannitol/(mannitol+premixed powder) mass fractions of 0%, 10%, 20%, 30%. The powder was then mixed thoroughly with glycerol at a powder to liquid ratio of 4 g/ml. After 24 h, the samples were removed from the mould and placed in the PBS solution for 2 days to dissolve the mannitol and form macropores.

Compressive Strength

For CS measurements, the paste was injected into cylindrical moulds and immersed in 50 ml PBS at 37° C. in a sealed beaker. Sample dimensions were diameter 6 mm and height 12 mm. After 24 h, the samples were removed from the moulds and placed in the PBS solution for 2 days to dissolve the mannitol and form macropores. Thereafter the maximum compressive stress until failure was measured using a universal testing machine.

Diametral Tensile Strength

For the diametral tensile strength (DTS) measurement, the samples measured 6 mm in diameter and 3 mm in height. The tensile strength was determined by loading the samples at 1 mm/min across a diameter producing tensile stresses perpendicular to the vertical plane passing through the center of the specimen. After each compressive test, the fracture load was recorded.

Density and Relative Porosity Measurements

The specimens (6 mm×12 mm) with various mannitol mass fractions were dried. Both apparent and true densities were calculated for each specimen, where apparent density included both the open and closed porosity in the volume of the sample, and true density included only the closed porosity in the volume of the structure. The bulk density or the apparent density of the specimens was calculated from the ratio of the specimen weight to the specimen volume. The volume was calculated by the specimen dimensions. The skeletal densities of the specimens were determined by the use of helium.

The results are set forth in Table 3:

TABLE 3

Setting time, compression strength and diametral tensile strength

| Mannitol Mass fraction (%) | Compression strength (MPa) | Diametral tensile strength (MPa) |
|---|---|---|
| 0 | 9.6 (1.2) | 1.91 (0.18) |
| 10 | 5.2 (0.7) | 0.73 (0.18) |
| 20 | 1.6 (0.17) | 0.36 (0.12) |
| 30 | 0.30 (0.07) | — |

Porosity

Figure 2:
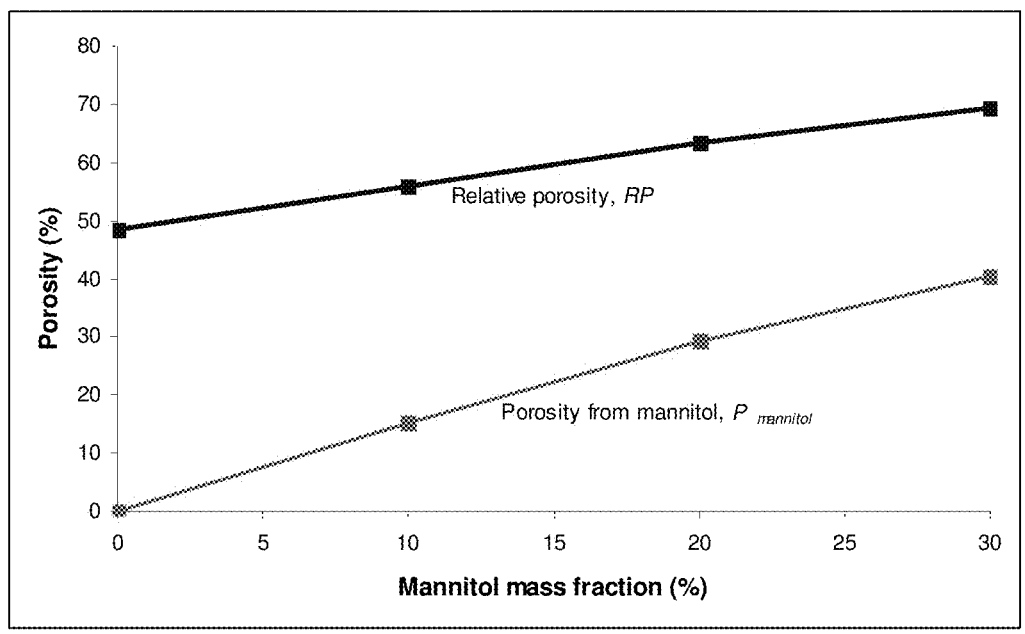
FIG. 2 shows the relative porosity and porosity from mannitol of premixed cement as a function of mannitol mass fraction, as described in Example 2.

Table 4 shows the bulk and true densities of the samples. Bulk density is found to range from 1.45 to 0.87 g/cm³. FIG. 2 shows the relative porosity and porosity from mannitol as a function of mannitol mass fraction.

TABLE 4

Density measurements of the premixed cement

| Mannitol mass fraction (%) | Bulk density (g/cm³) | Pycnometer density (g/cm³) |
|---|---|---|
| 0 | 1.45 (0.02) | 2.83 (0.001) |
| 10 | 1.23 (0.33) | 2.82 (0.003) |
| 20 | 1.03 (0.17) | 2.80 (0.002) |
| 30 | 0.87 (0.01) | 2.83 (0.006) |

The specific examples and embodiments described herein are exemplary only in nature and are not intended to be limiting of the invention defined by the claims. Further embodiments and examples, and advantages thereof, will be apparent to one of ordinary skill in the art in view of this specification and are within the scope of the claimed invention.

What is claimed is:

1. A non-aqueous hydraulic cement composition comprising a non-aqueous mixture of (a) β-tricalcium phosphate powder, (b) monocalcium phosphate powder, and (c) non-aqueous water-miscible liquid, wherein at least about 90% of the monocalcium phosphate powder has a grain size in a range of about 1-600 μm, wherein the monocalcium phosphate powder has grain sizes in each of the ranges of <100 μm, 100-200 μm, 200-400 μm, and 400-600 μm, and wherein the powder (weight) to liquid (volume) ratio is about 2.5-5.5.

2. The non-aqueous hydraulic cement composition of claim 1, wherein the powder (weight) to liquid (volume) ratio is about 3.5-5.

3. The non-aqueous hydraulic cement composition of claim 1, wherein at least about 95% of the monocalcium phosphate powder has said grain size.

4. The non-aqueous hydraulic cement composition of claim 1, wherein the weight ratio of (a) β-tricalcium phosphate powder to (b) monocalcium phosphate powder is from about 1:4 to about 4:1.

5. The non-aqueous hydraulic cement composition of claim 1, wherein the weight ratio of (a) β-tricalcium phosphate powder to (b) monocalcium phosphate powder is from about 2:3 to about 3:1.

6. The non-aqueous hydraulic cement composition of claim 1, wherein the β-tricalcium phosphate powder has a mean particle size of about 1-40 μm.

7. The non-aqueous hydraulic cement composition of claim 1, further comprising a porogen.

8. The non-aqueous hydraulic cement composition of claim 7, comprising about 5-30 weight percent of the porogen, wherein the porogen comprises a powder having a grain size in the range of 50-600 μm.

9. The non-aqueous hydraulic cement composition of claim 1, further comprising porous β-tricalcium phosphate granules.

10. The non-aqueous hydraulic cement composition of claim 1, wherein the monocalcium phosphate is anhydrous monocalcium phosphate.

11. The non-aqueous hydraulic cement composition of claim 1, wherein less than 5% of the monocalcium phosphate powder has a grain size larger than 600 μm.

12. The non-aqueous hydraulic cement composition of claim 1, wherein the monocalcium phosphate powder comprises monocalcium phosphate monohydrate powder.

13. The non-aqueous hydraulic cement composition of claim 1, wherein the pH of the cement composition is less than 6.0 and the cement composition forms Monetite upon setting.

14. A method of preparing a hardened cement, comprising contacting the non-aqueous hydraulic cement composition of claim 1 with a hydrating liquid or vapor.

15. The method of claim 14, wherein the hydrating liquid comprises water.

16. A hardened cement formed according to the method of claim 14.

17. The method of claim 14, wherein the non-aqueous hydraulic cement composition is injected in vivo and the hydrating liquid comprises a body fluid.

18. An article of manufacture comprising a container filled with the non-aqueous hydraulic cement composition of claim 1.

19. The article of manufacture of claim 18, wherein the container is a syringe.

20. The article of manufacture of claim 18, wherein the container is a vacuum package.

21. A kit comprising an article of manufacture according to claim 18 and a separately-contained quantity of hydrating liquid.

22. A non-aqueous hydraulic cement composition comprising a non-aqueous mixture of (a) β-tricalcium phosphate powder having a mean particle size of about 1-40 μm, (b) monocalcium phosphate monohydrate powder, wherein at least about 90% of the monocalcium phosphate monohydrate powder has a grain size in a range of about 1-600 μm and the monocalcium phosphate monohydrate powder has grain sizes in each of the ranges of <100 μm, 100-200 μm, 200-400 μm, and 400-600 μm, and (c) non-aqueous water-miscible liquid, wherein the weight ratio of (a) β-tricalcium phosphate powder to (b) monocalcium phosphate powder is from about 2:3 to about 3:1, the powder (weight) to liquid (volume) ratio is about 3.5-5, the pH of the cement composition is less than 6.0, and the cement composition forms Monetite upon setting.

* * * * *